United States Patent [19]
Chapel

[11] 3,941,573
[45] Mar. 2, 1976

[54] APPARATUS FOR REMOVING ANESTHETIC GASES

[76] Inventor: James Frederick Chapel, 900 Willowood No. 2, Denton, Tex. 76201

[22] Filed: May 2, 1974

[21] Appl. No.: 466,239

[52] U.S. Cl. .................... 55/316; 55/389; 55/518; 210/446; 128/188
[51] Int. Cl.² .......................................... B01D 50/00
[58] Field of Search ............ 55/316, 387, 389, 502, 55/518, 274; 210/446; 128/142.6, 146.2, 146.6, 191, 188

[56] References Cited
UNITED STATES PATENTS

| | | | |
|---|---|---|---|
| 1,866,659 | 7/1932 | Little, Jr. | 55/388 |
| 3,169,112 | 2/1965 | Nelson | 210/466 |
| 3,183,906 | 5/1965 | Moyat | 128/191 R |
| 3,283,479 | 11/1966 | Batzer | 55/316 |
| 3,406,501 | 10/1968 | Watkins | 55/316 |
| 3,555,787 | 1/1971 | Lustig | 55/316 |
| 3,557,534 | 1/1971 | Kennedy | 55/389 |
| 3,681,899 | 8/1972 | Grote | 55/518 |
| 3,713,273 | 1/1973 | Coffee | 55/389 |
| 3,815,752 | 6/1974 | Hoffman et al. | 55/387 |
| 3,867,936 | 2/1975 | Kelley | 128/188 |

FOREIGN PATENTS OR APPLICATIONS

| | | | |
|---|---|---|---|
| 1,964,739 | 6/1971 | Germany | 55/389 |

*Primary Examiner*—Bernard Nozick

[57] ABSTRACT

Apparatus is disclosed for removing medical anesthetic gases, after inhalation by a patient, in order to prevent these gases from being expelled into an operating room. In one embodiment, the apparatus includes a housing adapted to be connected into an anesthetic gas system, and a removable and disposable cartridge in the housing including at least two anesthetic gas adsorbent fillers. In other embodiments a disposable cartridge may be employed without a housing which can be readily connected into the anesthetic gas system.

11 Claims, 6 Drawing Figures

APPARATUS FOR REMOVING ANESTHETIC GASES

This invention relates to apparatus for removing anesthetic gases after inhalation by a patient in an operating room, and in one of its aspects to such an apparatus which includes a disposable gas adsorbent cartridge.

During the operating procedure, as a patient inhales and expels anesthetic gases, it is necessary that even small amounts of these gases be prevented from being expelled or exhausted in the operating room. This is because the physicians, nurses, and other personnel who are regularly involved in operating procedures are susceptible to various adverse physiological reactions caused by breathing small amounts of anesthetic gases in the operating room over a long period of time. Specifically, such effects include an increased rate of spontaneous abortion among female anesthesiologists and nurse-anesthetists, an increase in reticuleondothelial and lymphoid malignancies as causes of death among anesthesiologists of both sexes and a significant increase in birth defects in offspring of nurse-anesthetists [REF. Medical World News, 14, 24 (1973)]. Thus, there is a need for an adsorption device for adsorbing these gases as they are exhaled by the patient. It is preferred that such a device by simple and relatively inexpensive, and that it be easily inserted into the anesthesia system and easily removed therefrom when it is filled to capacity with adsorbed gases.

A disposable anesthesia adsorption apparatus has been provided by Dragerwerk AG of Germany which includes an adsorbent filler, such as activated carbon, in a metal canister. The metal canister is connected into the anesthesia system through rubber caps, similar to suction cups, mounted on each end of the canister. The placement and removal of the Dragerwerk canister is time consuming and because the canister is constructed as a sealed metal member, it is relatively expensive for an item which must be disposed of after but a few hours use. Also, the adsorbent filler compound in the Dragerwerk apparatus, which is activated carbon, only provides for about 5 hours of efficient anesthesia gas adsorption before it must be disposed of and this requires more frequent changing of the canister during use in the operating room than is desirable.

The principal object of the present invention is to provide an anesthesia gas removal system including a disposable gas adsorbent canister cartridge which provides for substantially longer use than the prior art devices discussed before it must be disposed of, and which is relatively simpler to replace and remove and relatively less expensive to manufacture. For this purpose, the apparatus of this invention includes a disposable cartridge made of a relatively inexpensive material such as cardboard or plastic and including a combination of adsorbent fillers which provides for longer use in service than the activated carbon adsorbent filler described with respect to the prior art. In one embodiment of this invention, the cartridge is mounted in a housing connected in the exhaust line of an anesthesia system and the housing is constructed so that it can be readily opened and closed to permit placement and removal of the cartridge including the adsorbent fillers. In other embodiments of the invention the cartridge can be directly connected into the anesthesia system by simple connecting means and the housing eliminated.

The adsorbent fillers of the disposable cartridge of this invention preferably are a combination of activated carbon and molecular sieve as hereinafter described in the ratio of quantities of from about 2:1 to 5:1 activated carbon to molecular sieve, and preferably in the ratio of about 3:1. Examples of anesthetic gases which may be adsorbed by the type of adsorbent fillers used by the present invention are chloroform, ethyl cloride, nitrous oxide, trichloroethylene, halothane, penthrane, and ethrane.

Referring to the drawings, wherein like reference numerals are used throughout to designate like parts, and wherein a preferred embodiment of the present invention is illustrated:

Figure 1:
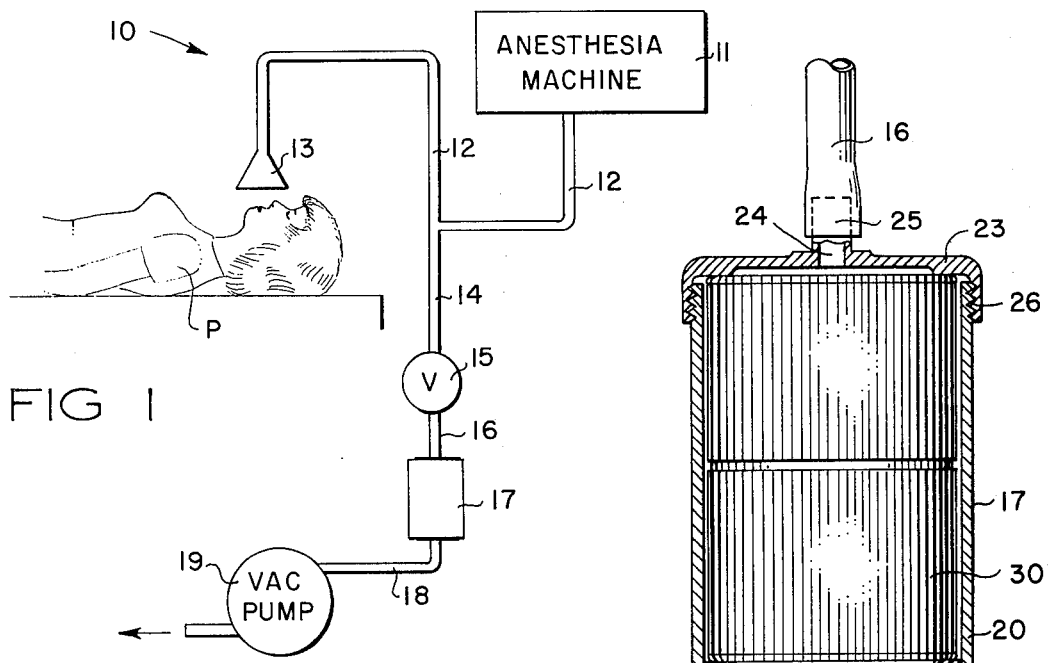
FIG. 1 is a schematic view of an anesthesia system utilizing the gas adsorbent apparatus of the present invention.

Referring to FIG. 1, an anesthesia system 10 is illustrated as including an anesthesia machine 11 for supplying anesthesia gas through a conduit 12 and face mask 13 to a patient P. Connected to conduit 12 is an exhaust conduit 14 which is connected through a valve 15 and conduit 16 to a cylindrical housing 17, in which the disposable cartridge of the present invention is mounted. Housing 17, which is substantially gas-tight, is connected in line between valve 15 and a vacuum pump 19 by a hose 18 so that when valve 15 is switched to provide for communication between conduit 14 and housing 17, gases from exhaling of patient P are drawn through conduit 14 and housing 17. As the patient is anesthetized, the anesthesiologist may "rebreathe" the patient by maintaining valve 15 closed until the patient has received sufficient anesthesia in which case valve 15 can be switched to permit dumping through housing 17.

Figure 2:
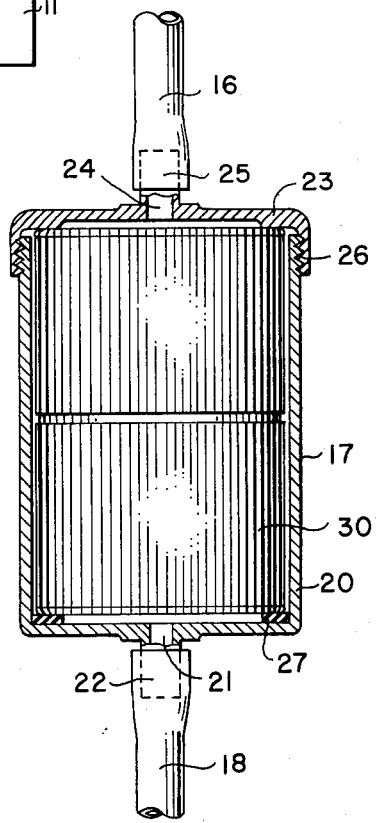
FIG. 2 is a partial sectional view illustrating one embodiment of this invention including a housing in which the disposable cartridge including the adsorbent fillers of this invention is mounted.

The details of cylinderical housing 17 are illustrated in FIG. 2. It includes a lower body section 20 which includes an opening 21 into which a suitable connector 22 is mounted which can be connected to a conduit or hose 18. Cylindrical housing 17 also includes a removable cover 23 at the top which includes an inlet opening 24 into which a suitable connector 25 is mounted which can be connected to conduit 16 so that when cover 23 is mounted on portion 20 of housing 17, a closed, gas-tight, integral housing is formed. Section 20 and cover 23 of cylindrical housing 17 may be made of metal or plastic threads 26 or other suitable connecting means may be provided between them to permit rapid connection and disconnection of the members. The connecting means may be any suitable mechanism for providing a quick disconnect when it is required to change the cartridge mounted in housing 17.

Also, a gasket 27 or other suitable seal means may be provided in the bottom of the interior of housing 17 to prevent anesthesia gases from by-passing the disposable gas adsorbent cartridge mounted in housing 17, and to be described.

Figure 3:
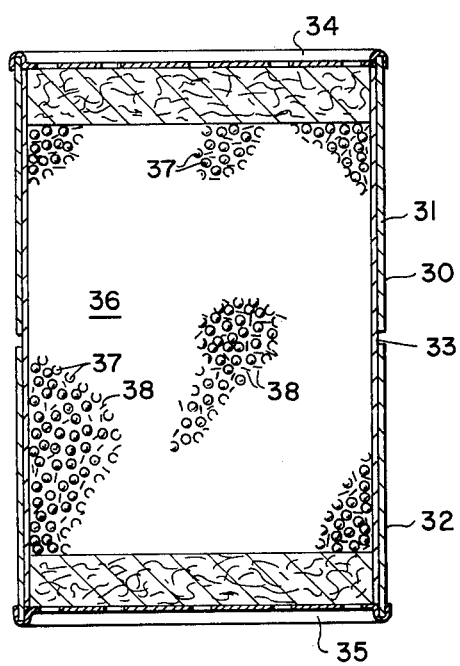
FIG. 3 is a sectional view of the disposable cartridge of FIG. 2.
Figure 4:
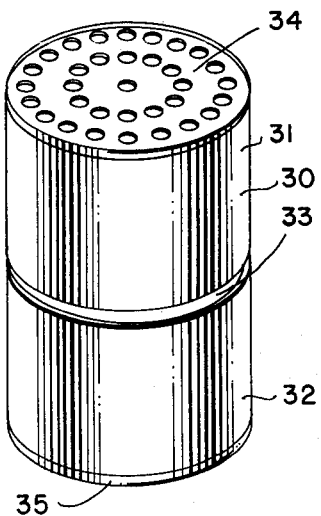
FIG. 4 is a front sectional view of the disposable cartridge of FIG. 2.

A disposable gas adsorbent cartridge 30 is disposed in housing 17 as illustrated in FIG. 2. The details of cartridge 30 are illustrated in FIGS. 3 and 4. Cartridge 30 is preferably made of cardboard or other relatively inexpensive and readily available material so that it is readily disposable, and includes an outer shell comprising two end cylindrical cardboard sections 31 and 32 telescoped over a central core cylindrical section 33, all preferably made of cardboard. Top and bottom end covers 34 and 35, which are perforated and preferably made of a light metal, such as tin or aluminum, are mounted at the ends of cartridge 30 with their edges lapped over the cylindrical cardboard sections as shown. The combination of cylindrical sections 31, 32 and 33, and end covers 34 and 35 form a cartridge with a hollow interior 36 in which the adsorbent fillers of the present invention are placed. Mounted in interior 36 of cartridge 30, each adjacent an end thereof, are filter pads 37 and 38 which may be most any conventional filter which permits the passage of air or other gases while preventing the passage of solid particles, such as the adsorbent fillers to be described.

In accordance with this invention, the interior 36 of cartridge 30, between filter pads 34 and 35, is substantially or completely filled with at least two adsorbent fillers which function to adsorb anesthesia gases that pass through cartridge 30. It is preferred that one of these fillers be activated carbon, represented by the generally sperical particles 37, and that the other be zealite or "molecular sieve", as represented by the smaller rectangular shaped particles 38.

The activated carbon functions as the major adsorbent and adsorbs anesthesia gases by surface absorption. The molecular sieve functions as a minor adsorbent and may be a sodium aluminum silicon hydrate with the statistical formula of:

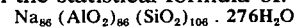
$$Na_{86}(AlO_2)_{86}(SiO_2)_{106} \cdot 276H_2O$$

It is preferred that the activated carbon particles have a particle size in the range of 6 to 30 U.S. Sieve Series and that they perferably be about 16 U.S. Sieve Series in size, and that the molecular sieve particles have a particle size in the range of one eighth inch to one sixteenth inch in size. It is also preferred that the ratio of the quantity of particles in cartridge 30 of activated carbon to molecular sieve be in the range of about 2:1 to about 5:1, with a preferred ratio of 3:1.

Figure 6:
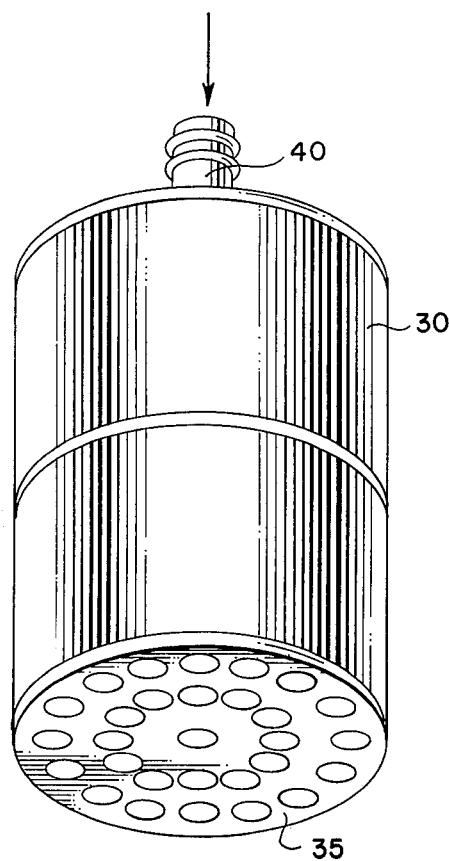
FIG. 6 is a perspective view of another embodiment of the present invention in which a disposable cartridge is provided which is exhausted to atmosphere.
Figure 5:
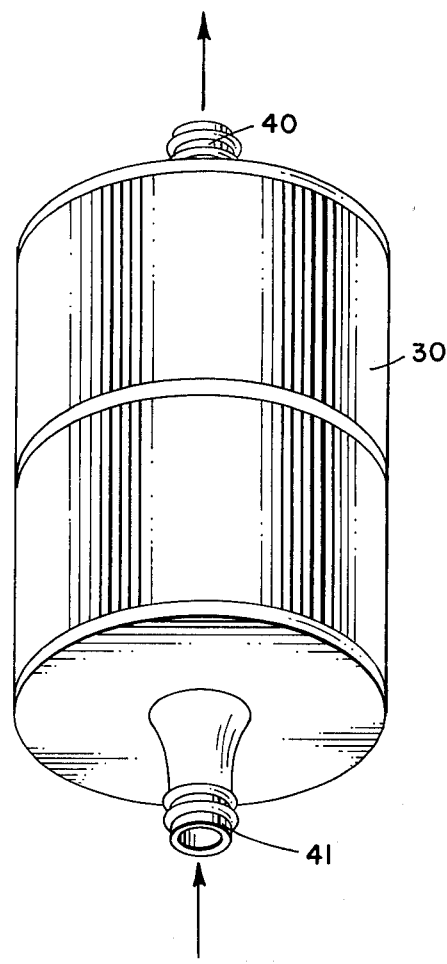
FIG. 5 is a perspective view of an embodiment of the present invention in which a disposable cartridge is employed without the separate housing.

In FIG. 5, cartridge 30 is illustrated with the ends closed and nipples 40 and 41 mounted thereon to provide connection to hoses 16 and 18, so that a disposable cartridge is provided without the necessity of housing 17. In FIG. 6, the illustrated lower end of cartridge 30 is perforated and open to atmosphere and the illustrated top end includes nipple 40 for connection to hose 16. This embodiment may be employed in single patient use where less back pressure in the system is encountered so that the patient expiratory pressure is sufficient to cause gases to vent through cartridge 30.

Thus, by use of disposable cartridge including two adsorbent fillers, the period of use of each cartridge is extended to an average of about twelve hours, at which time the cartridge can be readily replaced. Since the fillers used include particles that are sperically shaped and particles that are relatively smaller and in the shape of small needles, the quantity of adsorbent fillers in a given sized cartridge can be increased since the smaller particles can be in the voids or spaces between the larger particles. Thus, the available surface area for adsorption of anesthetic gases can be increased without increasing the size or comlexity of the cartridge, to provide a relatively longer period of usage.

From the foregoing, it will be seen that this invention is one well adapted to attain all of the ends and objects hereinabove set forth, together with other advantages which are obvious and which are inherent to the apparatus.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

What is claimed is:

1. A disposable cartridge for use in adsorbing anesthesia gases in an anesthesia system, comprising:
    a cylindrical outer shell made of a disposable material including at least one perforated end member;
    two filter means disposed in said shell each being adjacent one of the ends to permit the passage of a gas through said cartridge while preventing the passage of solid particles; and
    at least two adsorbent fillers for adsorbing anesthesia gases disposed in said shell between said filter means so that said fillers are mixed together, one of said adsorbent fillers being substantially spherical shaped activated carbon and the other of said adsorbent fillers being molecular sieve shaped of a configuration that permits it to lie in voids between said spherical shaped fillers, said fillers being of sufficient quantity in said shell to provide for a relatively long useful life for said cartridge when used to adsorp anesthesia gases evacuated by a human patient while permitting effective evacuation of the respiratory system of such a patient.

2. The cartridge of claim 1 wherein said shell is made of cardboard.

3. The cartridge of claim 1 wherein each end of the cartridge is perforated.

4. The cartridge of claim 1 wherein one of the ends of the cartridge is perforated and the other includes a nipple connector.

5. The cartridge of claim 1 wherein each of the ends of the cartridge includes a nipple connector.

6. The cartridge of claim 1 wherein the quantity of said activated carbon and said molecular sieve in said cartridge is in a ratio of about 2:1 to about 5:1 activated carbon to molecular sieve.

7. The cartridge of claim 6 wherein said ratio is about 3:1 activated carbon to molecular sieve.

8. The cartridge of claim 1 wherein said shell comprises a central core section and two end sections telescoped over said central core section.

9. The cartridge of claim 8 wherein said central core and end sections are made of cardboard.

10. A disposable cartridge for use in adsorbing anesthesia gases in an anesthesia system, comprising:
    a cylindrical outer shell made of a disposable material including perforated end members;
    two filter means disposed in said shell each being adjacent one of the end members to permit the passage of a gas through said cartridge while preventing the passage of solid particles; and at least two adsorbent fillers for adsorbing anesthesia gases disposed in said shell between said filter means so that said fillers are mixed together, one of said adsorbent fillers being substantially spherical shaped and having a particle size of about 6 to about 30 U.S. Sieve Series, and the other of said adsorbent fillers being shaped of a configuration that permits it to lie in voids between said spherical shaped fillers, and having a particle size in the range of about one-eight to about one-sixteenth inch in size, the quantity of said fillers in said shell being in the ratio of about 2:1 to about 5:1 of the substantially spherically shaped filler to the other filler, and sufficient to provide effective adsorption of anesthesia gas in an anesthesia system for up to about 12 hours without creating excessive back pressures on the respiratory system of a patient.

11. The cartridge of claim 10 wherein said one of said fillers is activated carbon and the other is molecular sieve.

* * * * *

UNITED STATES PATENT AND TRADEMARK OFFICE
CERTIFICATE OF CORRECTION

PATENT NO. : 3,941,573
DATED : March 2, 1976
INVENTOR(S) : James Frederick Chapel It is certified that error appears in the above-identified patent and that said Letters Patent are hereby corrected as shown below:

Col. 1, Line 26, "by" should be -- be --
Col. 2, Line 47, Insert -- As the patient is anesthetized, the anesthesiologist may "rebreathe" the patient by maintaining valve 15 closed until the patient has received sufficient anesthesia in which case valve 15 can be switched to permit dumping through housing 17. --

Col. 3, Line 41, "perferably" should be -- preferably --
Col. 3, Line 42, "molecular sieve" should be -- "molecular sieve" --

Signed and Sealed this

Third Day of August 1976

[SEAL]

Attest:

RUTH C. MASON
Attesting Officer

C. MARSHALL DANN
Commissioner of Patents and Trademarks